United States Patent
Medina et al.

(10) Patent No.: US 10,902,586 B2
(45) Date of Patent: Jan. 26, 2021

(54) AUTOMATED VISUAL RECOGNITION OF A MICROCALCIFICATION

(71) Applicant: International Business Machines Corporation, Armonk, NY (US)

(72) Inventors: Ramon Oswaldo G. Medina, Tecalitlán (MX); Juan Manuel A. Vega, Zapopan (MX)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 141 days.

(21) Appl. No.: 15/973,826

(22) Filed: May 8, 2018

(65) Prior Publication Data
US 2019/0347787 A1 Nov. 14, 2019

(51) Int. Cl.
*G06T 7/00* (2017.01)
*G06K 9/62* (2006.01)
*G16H 30/40* (2018.01)

(52) U.S. Cl.
CPC .......... *G06T 7/0012* (2013.01); *G06K 9/6256* (2013.01); *G16H 30/40* (2018.01); *G06K 2209/05* (2013.01); *G06T 2207/10116* (2013.01); *G06T 2207/20024* (2013.01); *G06T 2207/20076* (2013.01); *G06T 2207/20081* (2013.01); *G06T 2207/30068* (2013.01)

(58) Field of Classification Search
CPC .......... G06T 7/0012; G06T 2207/20076; G06T 2207/30068; G06T 2207/20024; G06T 2207/20081; G06T 2207/10116; G06K 9/6256; G06K 2209/05; G16H 30/40; G16H 50/30; G16H 50/20
See application file for complete search history.

(56) References Cited

U.S. PATENT DOCUMENTS

| | | | |
|---|---|---|---|
| 6,137,898 A | 10/2000 | Broussard et al. | |
| 7,054,473 B1 | 5/2006 | Roehrig et al. | |
| 7,383,237 B2 | 6/2008 | Zhang et al. | |
| 7,899,228 B2 | 3/2011 | Chen et al. | |
| 8,164,039 B2 | 4/2012 | Bovik et al. | |
| 8,238,637 B2 | 8/2012 | Ratner et al. | |
| 8,751,530 B1* | 6/2014 | Ioffe | G06F 16/583 707/772 |

(Continued)

FOREIGN PATENT DOCUMENTS

CN 102663410 B 2/2014

OTHER PUBLICATIONS

Fung et al., "Addressing image variability while learning classifiers for deteting clusters of micro-calcifications" Siemens Medical Solutions, 8 pages, https://pdfs.semanticscholar.org/c964/fc7f6a1fa1d183a4ce46136e9b8db4df4c8a.pdf.

(Continued)

*Primary Examiner* — Mazda Sabouri
(74) *Attorney, Agent, or Firm* — Cantor Colburn LLP; Jason Sosa

(57) ABSTRACT

A computer-implemented method includes receiving an image representing a patient. A filter is applied to the image to produce a filtered image. The filtered image is submitted to a visual recognition tool. A score of the image is determined by the visual recognition tool, based on the filtered image, where the score indicates a likelihood that an abnormality appears in the image.

11 Claims, 8 Drawing Sheets

(56) References Cited

U.S. PATENT DOCUMENTS

| | | | |
|---|---|---|---|
| 9,122,897 | B2 | 9/2015 | Hernandez-Cisneros |
| 9,305,204 | B2 | 4/2016 | Mukhopadhyay et al. |
| 2004/0184647 | A1* | 9/2004 | Reeves ............... G06T 3/0075 382/131 |
| 2005/0100208 | A1* | 5/2005 | Suzuki ............... G06T 5/007 382/157 |
| 2015/0196265 | A1 | 7/2015 | Suzuki |
| 2017/0061607 | A1* | 3/2017 | Eskandari ............ G06T 7/11 |
| 2017/0309021 | A1* | 10/2017 | Barnes ............... G06T 7/0012 |
| 2018/0218496 | A1* | 8/2018 | Sinai ................ G06T 7/0012 |
| 2018/0315193 | A1* | 11/2018 | Paschalakis .......... G06T 7/0016 |
| 2019/0057500 | A1* | 2/2019 | Vega ................. G06K 9/6218 |
| 2019/0122073 | A1* | 4/2019 | Ozdemir .............. G06N 20/00 |
| 2019/0192229 | A1* | 6/2019 | Berlin ............... A61B 34/20 |

OTHER PUBLICATIONS

Machado de Oliveira et al, "Diagnostic Support System for the Detection of Microcalcifications in Digital Mammograms" 11 pages., http://www.abepro.org.br/biblioteca/ENEGEP2012_TN_STP_162_947_21082.pdf.

Zhang et al. "A Hybrid Image Filtering Method for Computer-Aided Detection of Microcalcification Clusters in Mammograms", Journal of Medical Engineering, vol. 2013, Article ID 615254, 8 pages, 2013.

Agrawal, Praful et al. "Saliency based mass detection from screening mammograms", Abstract Only, retrieved at: https://www.sciencedirect.com/science/article/pii/S0165168413004982; ScienceDirect; Signal Processing, vol. 99, Jun. 2014; 3 pgs.

Arikidis, Nikkolaos S. "Size-adapted microcalcification segmentation in mammography utilizing scale-space signatures", Abstract Only, retrieved at: https://www.sciencedirect.com/science/article/abs/pii/S0895611109001591; ScienceDirect, Computerized Medical Imaging and Graphics, vol. 34, Issue 6, Sep. 2010, 4 pgs.

Deshmukh K.C. et al. "Generalized Measures of Fuzzy Entropy and their Properties", World Academy of Science, Engineering and Technology 56; 2011; pp. 994-998.

Dheeba, J. et al. "A Swarm Optimized Neural Network System for Classification of Microcalcification in Mammograms", Abstract Only, Journal of Medical Systems, Oct. 2012, vol. 3, Issue 5,; Original Paper; First Online Sep. 23, 2011; retrieved at: https://link.springer.com/article/10.1007/s10916-011-9781-3; 8 pgs.

Hooda, D. S. "On generalized measures of fuzzy entropy" Mathematica Slovaca, vol. 54 (2004), No. 3, URL: http://dml.cz/dmlcz/131239; cover, pp. 315-325.

Hornsby, Adam N. et al. "Improved classification of mammograms following idealized training", Abstract Only, Retrieved at: https://www.sciencedirect.com/science/article/abs/pii/S2211368114000321; Journal of Applied Research in Memory and Cognition, vol. 3, Issue 2, Jun. 2014; 3 pgs.

Jen, Chun-Chu et al. "Automatic detection of abnormal mammograms in mammographic images", Abstract Only, retrieved at: https://www.sciencedirect.com/science/article/pii/S095741741400760X; Expert Systems with Applications, vol. 42, Issue 6, Apr. 15, 2015, 3 pgs.

Mohanalin, Beenamol "A novel automatic microcalcification detection technique using Tsallis entropy & a type II fuzzy index", Abstract Only, retrieved at: https://www.sciencedirect.com/science/article/pii/S0898122110006024; ScienceDirect; Computers & Mathematics with Applications vol. 60, Issue 8, Oct. 2010, 12 pgs.

Oliver, Arnau et al. "Automatic microcalcification and cluster detection for digital and digitised mammograms", Abstract Only, retrieved at: https://www.sciencedirect.com/science/article/abs/pii/S0950705111002577; ScienceDirect; Knowledge-Based Systems, vol. 28, Apr. 2012, 3 pgs.

Pal, Mahesh "Fuzzy Entropy-based feature selection for classification of hyperspectral data" Georspatial World, Mar. 19, 2012; 7 pgs.

Papadopoulos, A. et al. "Improvement of microcalcification cluster detection in mammography utilizing image enhancement techniques", Abstract Only, retrieved at: https://www.sciencedirect.com/science/article/abs/pii/S0010482508001042; Computers in Biology and Medicine, vol. 38, Issue 10, Oct. 2008, 3 pgs.

Pasha, Einollah et al. "Fuzzy Entropy as Cost Function in Image Processing" Proceedings of the 2nd IMT-GT Regional Conference on Mathematics, Statistics and Applications; Jun. 13-15, 2006; cover and pp. 1-8.

Pereira, Danilo Cesar et al. "Segmentation and detection of breast cancer in mammograms combining wavelet analysis and genetic algorithm", Abstract Only; retrieved at:https://www.sciencedirect.com/science/article/abs/pii/S0169260714000261; Computer Methods and Programs in Biomedicine; vol. 114, Issue 1, 3 pgs.

Servulo de Oliveira et al. "Classification of breast regions as mass and non-mass based on digital mammograms using taxonomic indexes and SVM", Computers in Biology and Medicine; 57; (2015) pp. 42-53.

Tao, Wen-Bing et al. "Image segmentation by three-level thresholding based on maximum fuzzy entropy and genetic algorithm", Abstract Only, ScienceDirect; retrieved at: https://www.sciencedirect.com/science/article/abs/pii/S0167865503001661; Pattern Recognition Letters vol. 24, Issue 16, Dec. 2003; 3 pgs.

Tortajada, Meritxell et al. "Breast peripheral area correction in digital mammograms", Abstract Only, Computers in Biology and Medicine, vol. 50, Jul. 1, 2014; retrieved at: https://www.sciencedirect.com/science/article/abs/pii/S0010482514000730; 3 pgs.

Triana, Nayid et al. "Computer-Aided Detection of Microcalcifications in Digital Mammograms to Support Early Diagnosis of Breast Cancer", Abstract Only, retrieved at: https://link.springer.com/chapter/10.1007%2F978-3-642-38637-4_30; Conference Paper, IWINAC 2013; Natural and Artificial Models in Computation and Biology; 6 pgs.

Vallez, Noelia et al. "Breast density classification to reduce false positives in CADe systems", Abstract Only, retrieved at: https://www.sciencedirect.com/science/article/abs/pii/S0169260713003441; Science Direct, Computer Methods and Programs in Biomedicine, vol. 113, Issue 2, Feb. 2014; 3 pgs.

Verma, Rajkumar et al. "On Generalized Exponential Fuzzy Entropy", World Academy of Science, Engineering and Technology 60; 2011; retrieved at: https://www.researchgate.net/publication/234062704; cover, pp. 1402-1405.

Wojtowicz, T. "An improvement in fuzzy entropy edge detection for X-ray imaging", Abstract Only, retrieved at: http://yadda.icm.edu.pl/yadda/element/bwmeta1.element.baztech-article-BUJ8-0023-0008; Schedae Informaticae 2011, vol. 20, 2 pgs.

\* cited by examiner

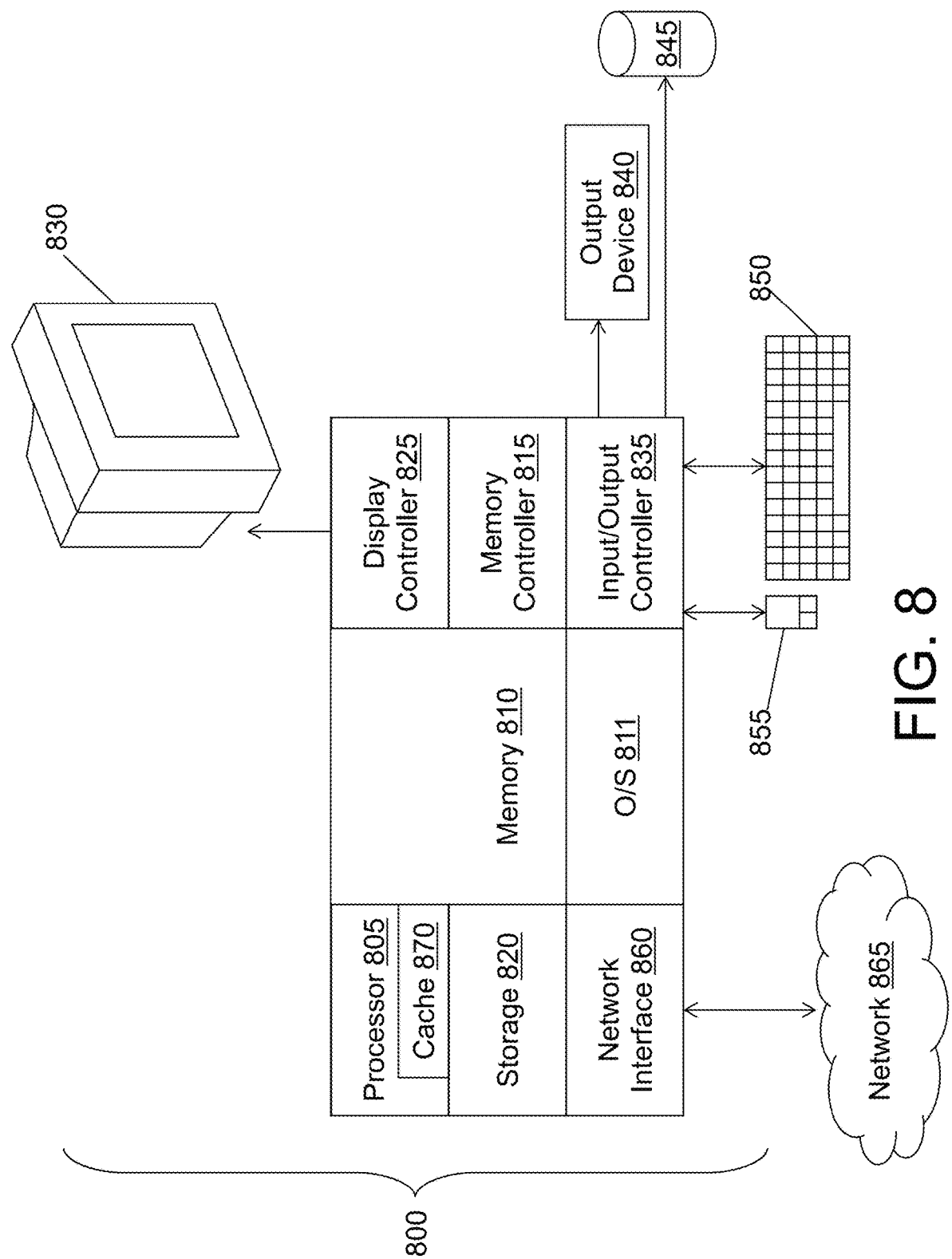

AUTOMATED VISUAL RECOGNITION OF A MICROCALCIFICATION

BACKGROUND

The present invention relates to visual recognition and, more specifically, to automated visual recognition of a microcalcification.

A mammogram is a low-dose X-ray used to see inside breasts, often as part of a screening for breast cancer. A medical professional can manually analyze a mammogram to identify a microcalcification in a breast. A microcalcification is a mineral deposit, which can either be benign or cancerous. Thus, a microcalcification identified in a mammogram image of a patient can be an indication that a medical professional should follow-up with that patient for further testing or treatment.

SUMMARY

Embodiments of the present invention are directed to a computer-implemented method for screening mammograms. A non-limiting example of the computer-implemented method includes receiving an image representing a patient. A filter is applied to the image to produce a filtered image. The filtered image is submitted to a visual recognition tool. A score of the image is determined by the visual recognition tool, based on the filtered image, where the score indicates a likelihood that an abnormality appears in the image.

Embodiments of the present invention are directed to a system for screening mammograms. A non-limiting example of the system includes a memory having computer-readable instructions and one or more processors for executing the computer-readable instructions. The computer-readable instructions include receiving an image representing a patient. Further according to the computer-readable instructions, a filter is applied to the image to produce a filtered image. The filtered image is submitted to a visual recognition tool. A score of the image is determined by the visual recognition tool, based on the filtered image, where the score indicates a likelihood that an abnormality appears in the image.

Embodiments of the invention are directed to a computer-program product for screening mammograms, the computer-program product including a computer-readable storage medium having program instructions embodied therewith. The program instructions are executable by a processor to cause the processor to perform a method. A non-limiting example of the method includes receiving an image representing a patient. Further according to the method, a filter is applied to the image to produce a filtered image. The filtered image is submitted to a visual recognition tool. A score of the image is determined by the visual recognition tool, based on the filtered image, where the score indicates a likelihood that an abnormality appears in the image.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

FIGS. 5A-5B illustrate an example application of a mathematical morphological filter, according to some embodiments of the invention;

FIG. 8 is a block diagram of a computer system for implementing some or all aspects of the screening system, according to some embodiments of this invention.

Figure 1:
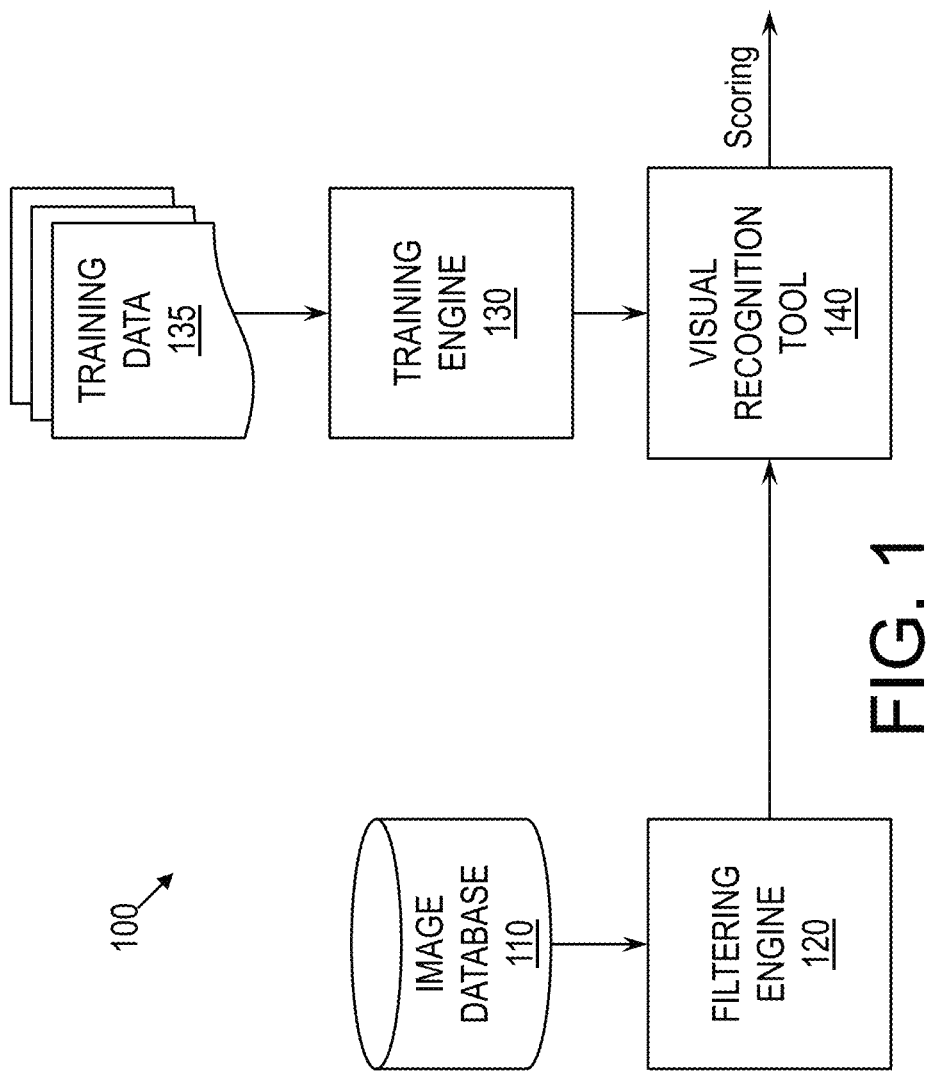
FIG. 1 is a block diagram of a screening system for identifying a microcalcification, according to some embodiments of the invention.

The diagrams depicted herein are illustrative. There can be many variations to the diagram or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

In the accompanying figures and following detailed description of the disclosed embodiments, the various elements illustrated in the figures are provided with two- or three-digit reference numbers. With minor exceptions, the leftmost digit(s) of each reference number correspond to the figure in which its element is first illustrated.

DETAILED DESCRIPTION

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

The following definitions and abbreviations are to be used for the interpretation of the claims and the specification. As used herein, the terms "comprises," "comprising,"

"includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" may be understood to include any integer number greater than or equal to one, i.e. one, two, three, four, etc. The terms "a plurality" may be understood to include any integer number greater than or equal to two, i.e. two, three, four, five, etc. The term "connection" may include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

Turning now to an overview of technologies that are more specifically relevant to aspects of the invention, while a mammogram is a useful tool, oftentimes the workload of a medical facility does not enable medical professionals to review mammogram images in a timely manner. For women within a certain age range, an annual mammogram is recommended. Thus, a medical facility may have hundreds or thousands of mammograms to review at a given time. A microcalcification that is visible in a mammogram image may go unidentified while that mammogram image waits in line for review by a medical professional. As a result, a patent with a potentially cancerous microcalcification may not get the attention needed within a reasonable time.

Turning now to an overview of the aspects of the invention, one or more embodiments of the invention address the above-described shortcomings of the prior art by providing an automated mechanism for screening mammogram images to determine whether the mammogram images show microcalcifications. Specifically, according to some embodiments of the invention, a visual recognition tool is trained with positive and negative images, where a positive image is known to show a microcalcification and a negative image is known not to show a microcalcification. Each mammogram image to be screened may be passed through a filter, such as a hybrid filter, and then submitted to the trained visual recognition tool. The visual recognition tool may thus determine whether the mammogram image shows a microcalcification.

The above-described aspects of the invention address the shortcomings of the prior art by enabling mammogram images to be screened automatically, without intervention by a medical professional. As a result, mammogram images deemed to show microcalcifications, or deemed likely to show microcalcifications, may be prioritized for analysis by medical professionals. The order of mammogram analysis by human medical professionals may then be based on this prioritization, so that patients with high risk are considered sooner than those with lower risk. In summary, embodiments of the invention are screening systems incorporating an improved visual recognition tool for spotting microcalcifications, where the visual recognition tool is improved, at least in part, through the use of training and the use of the filter.

Turning now to a more detailed description of aspects of the present invention, FIG. 1 is a block diagram of a screening system 100, according to some embodiments of the invention. Generally, the screening system 100 may input a mammogram image and determine whether that mammogram image shows a microcalcification. Specifically, for instance, the screening system 100 may determine a score, which may be interpreted as a probability or likelihood that the mammogram shows a microcalcification. In some embodiments of the invention, a threshold score is established, and mammogram images with scores meeting the threshold score may be flagged. In practice, for example, the screening system 100 may receive a plurality of mammogram images, each representing a patient, and the screening system 100 may score each mammogram image. Thus, a medical professional may prioritize the mammogram images and respective patients based on the scores.

As shown in FIG. 1, the screening system 100 may include an image database 110, a filtering engine 120, a training engine 130, and a visual recognition tool 140. Generally, the image database 110 may maintain a plurality of mammogram images to be screened, the filtering engine 120 may apply a filter to the plurality of images, the training engine 130 may train the visual recognition tool 140 with training data 135 that includes known images, and the visual recognition tool 140 may then score each of the plurality of images according to the likelihood of a microcalcification being shown. Each of these components may include hardware, software, or a combination of both. For example, and not by way of limitation, each of these components may be implemented in software or may be a specialized hardware circuit.

Various visual recognition tools known in the art may be used as the visual recognition tool 140 For example, and not by way of limitation, the visual recognition tool of IBM Watson®, from International Business Machines®, may be used. The visual recognition tool 140 may be trainable based on training data 135, which may include a plurality of positive images and a plurality of negative images. The positive images may be tagged as positive, such that the visual recognition tool 140 recognizes that the positive images contain a characteristic sought to be recognized. Analogously, the negative images may be tagged as negative, such that the visual recognition tool 140 recognized that the negative images lack a characteristic sought to be recognized. As a result of analyzing the training data 135, the visual recognition tool 140 may be enabled to recognize the characteristic in question. More specifically, for instance, the visual recognition tool 140 may be able to output a score, such as a probability, indicating the likelihood that the characteristic exists in an image. Thus, according to some embodiments of the invention, after training, the visual recognition tool 140 takes a mammogram image as input and outputs a corresponding score.

It will be understood that, although this disclosure describes embodiments of the invention as applicable to mammogram images, the screening system 100 may be used for screening in various applications. For example, and not by way of limitation, the screening system 100 may be used to examine images of irises to identify abnormalities associated with diabetes. In that case, rather than mammogram images, an embodiment of the invention may use images of irises. It will be understood by one skilled in the art the type of images used may be based on the purpose of the screening system 100, and that embodiments of the invention may be used in various applications for recognizing abnormalities.

Figure 2:
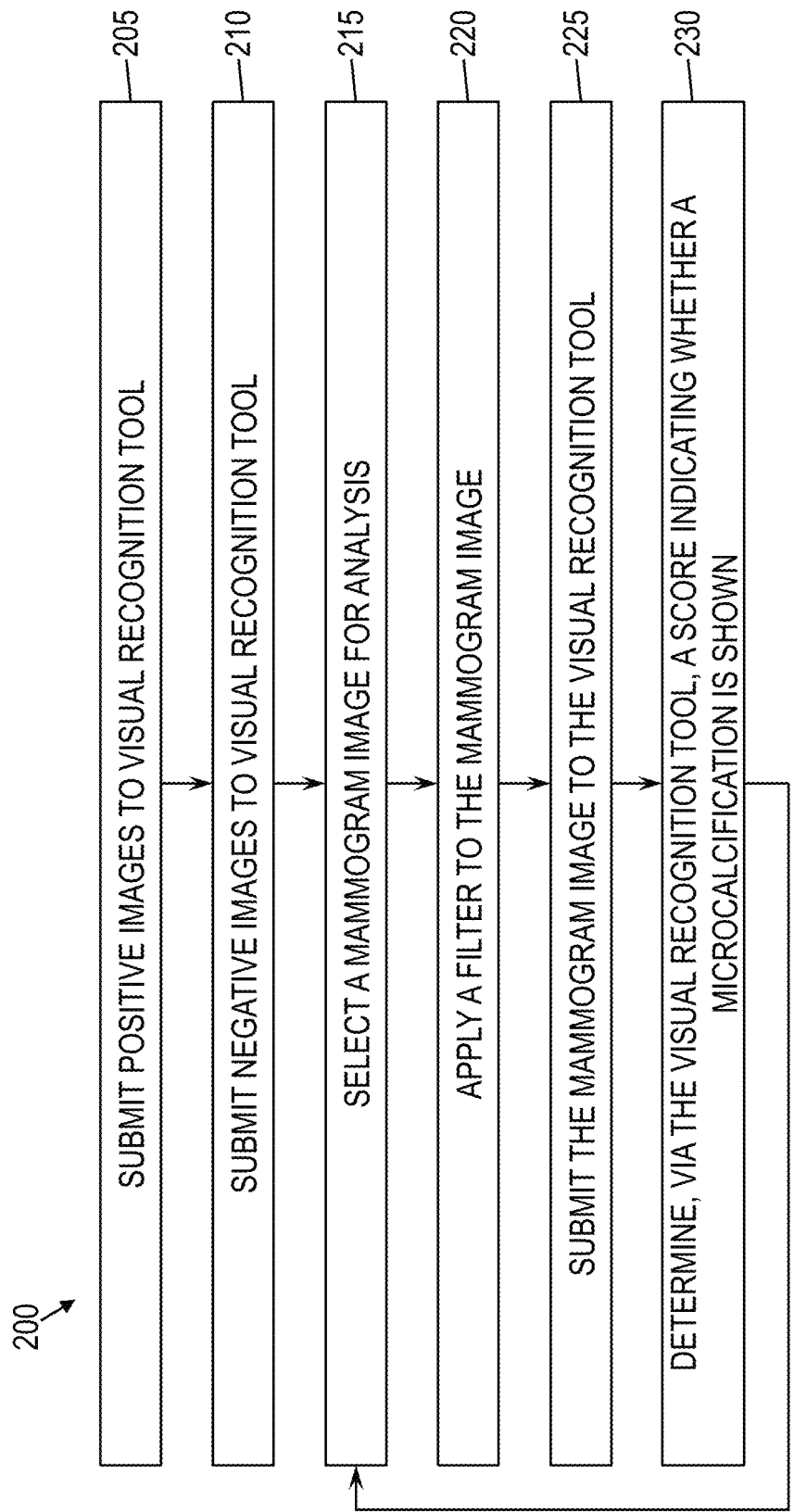
FIG. 2 is a flow diagram of a method of screening mammogram images using visual recognition, according to some embodiments of the invention.

FIG. 2 is a flow diagram of a method 200 of screening mammogram images using visual recognition, according to some embodiments of the invention. The method 200 may include two parts. In the first part, the visual recognition tool 140 may be trained to recognize microcalcifications based on training data 135. This part of the method 200 spans blocks 205-210 of the method 200, described below. In the second part, a mammogram image may be inputted into the screening system 100, and the screening system 100 may determine whether the mammogram image shows a microcalcification, by way of the trained visual recognition tool 140. For instance, the visual recognition tool 140 may determine a confidence level (e.g., a percentage) as to whether a microcalcification is present in the mammogram image. This part of the method 200 spans the remainder of the method blocks, beginning at block 215.

As shown, at block 205, a plurality of positive images may be submitted to the visual recognition tool 140, where each of the positive images includes a microcalcification. These positive images may be, for example, mammogram images that have been examined by one or more medical professionals trained to recognize microcalcifications. As such, it may be known that the positive images each show a microcalcification. For example, and not by way of limitation, at least fifty positive images may be submitted. The submission may include an indication that the positive images are positive for microcalcification.

At block 210, a plurality of negative images may be submitted to the visual recognition tool 140, where each of the negative images lacks a microcalcification. These negative images may be, for example, mammogram images that have been examined by a medical professional trained to recognize microcalcifications. As such, it may be known that none of the negative images shows a microcalcification. For example, and not by way of limitation, at least fifty negative images may be submitted. The submission may include an indication that the negative images are negative for microcalcification.

Together, the positive images and the negative images may make up the training data 135, with which the visual recognition tool 140 is trained. As a result of the submissions of positive and negative images, the visual recognition tool 140 may be trained to recognize microcalcifications. In some embodiments of the invention, the training in blocks 205-210 is performed by the training engine 130.

At block 215, which begins the second part of the method 200, a mammogram image may be selected for analysis. In some embodiments of the invention, the mammogram image is selected from the image database 110. The image database 110 may take various formats, such as a relational database or simply a folder for storage of the mammogram images as files. The image database 110 may be populated by one or more medical facilities, such that the mammogram images represent patients on whom mammograms have been performed. Thus, the selected mammogram image may represent a patient. In some embodiments of the invention, an X-ray device is incorporated into the screening system 100 or is in communication with the screening system 100, such that, upon capture of a mammogram image, that mammogram image is automatically stored in the image database 110.

Although the method 200 takes as input a single mammogram image at block 215, this second part of the method 200 may be performed repeatedly or may be performed in parallel on a batch of mammogram images to screen a plurality of mammogram images in total. To illustrate this, FIG. 2 includes a loop from the end of the method 200 back to block 215.

At block 220, a filter may be applied to the mammogram image. For instance, application of the filter may be performed by the filtering engine 120. Generally, the filter may be an image filter that enhances features and reduces noise in the mammogram image. For example, and not by way of limitation, the filter may be a mathematical morphological filter or an entropy filter. In some embodiments of the invention, the filter is a hybrid filter that incorporates both a mathematical morphological filter and an entropy filter. An example of such a hybrid filter will be described in more detail below, with reference to FIG. 3.

As shown in FIG. 2, at block 225, the mammogram image may be submitted to the visual recognition tool 140. At this point, if a filter is being used, the mammogram image may have already been through the filter and, as such, may already be a filtered image. Thus, the mammogram image submitted to the visual recognition tool 140 may be a filtered mammogram image.

At block 230, the visual recognition tool 140 may determine a score indicating whether the mammogram image shows a calcification. This determination may be made based on the training of the visual recognition tool 140 on the training data 135 of both positive and negative images. The score may represent a likelihood or confidence level as to whether a macrocalcification is present in the mammogram image. In some embodiments of the invention, if the score exceeds a threshold, then the visual recognition tool flags the mammogram image, such as by alerting that the mammogram image is likely to show a microcalcification.

Block 215 through 230 of the method 200 may be repeated as needed to analyze each mammogram image desired to be screened for microcalcifications.

Figure 3:
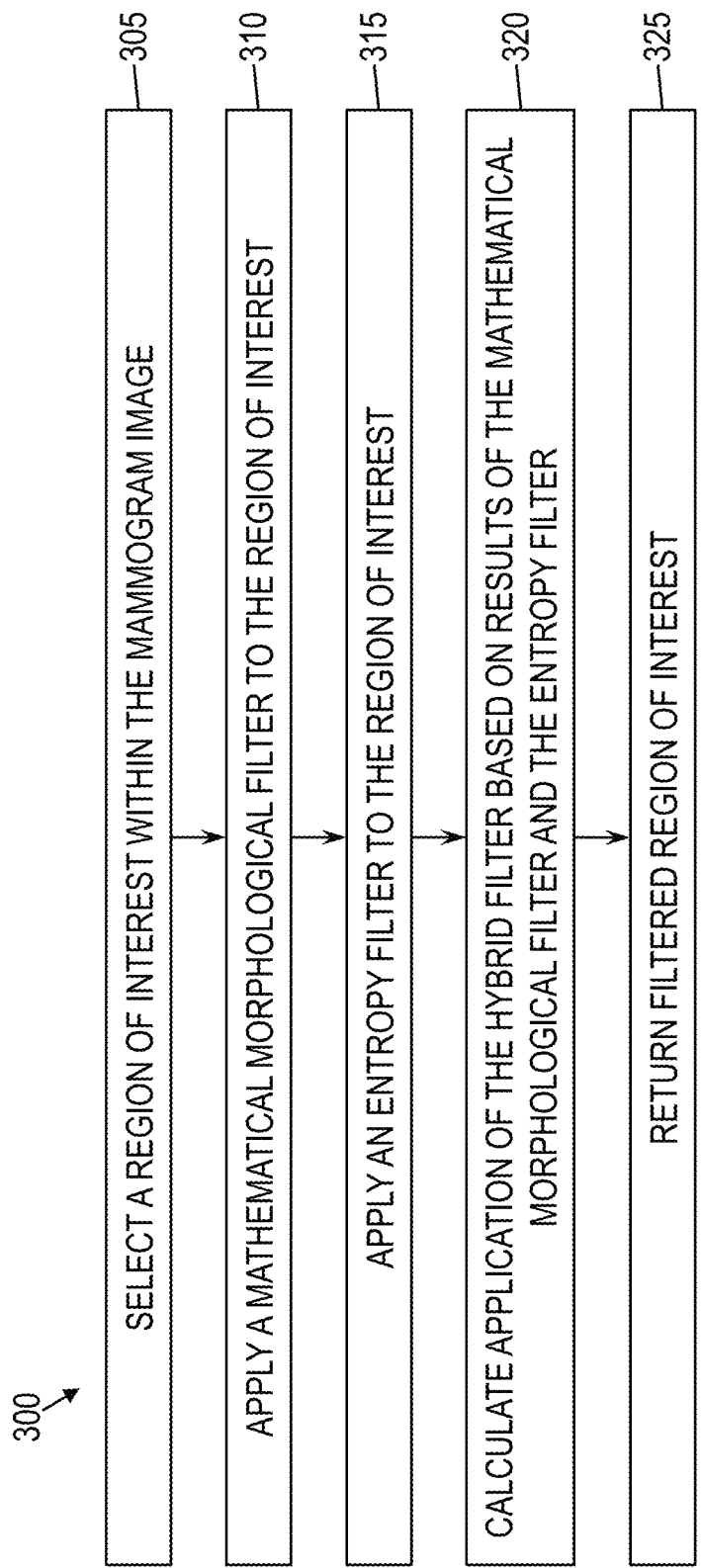
FIG. 3 is a flow diagram of a method of applying a hybrid filter to a mammogram image, according to some embodiments of the invention.

FIG. 3 is a flow diagram of a method 300 of applying a hybrid filter to a mammogram image, according to some embodiments of the invention. As discussed above, this method 300 may be performed at block 220 of the method 200 of recognizing a microcalcification. In some embodiments of the invention, the hybrid filter may be applied by combining two or more or more filters, such as by taking an average of the result of the two or more filters. For example, and not by way of limitation, these two or more filters may be a mathematical morphological filter and an entropy filter, as described below.

At block 305, a region of interest may be selected within the mammogram image. For example, and not by way of limitation, the region of interest may be a portion of the mammogram image, which may be 256 by 256 pixels or some other size deemed by a designer to meet accuracy and efficiency goals.

The region of interest may be a region of the mammogram image that is suspected to have a microcalcification. In some embodiments of the invention, the region of interest is associated with the mammogram image prior to this operation. For example, when the mammogram image is submitted to the image database 110, a region of interest may be specified, such as by a medical professional. In some embodiments of the invention, when no region of interest is known for the mammogram image, the entire mammogram image may be deemed to be the region of interest, or the mammogram image may be divided into two or more regions of interest, and each region of interest in the mammogram image may be filtered as described below.

Figure 4:
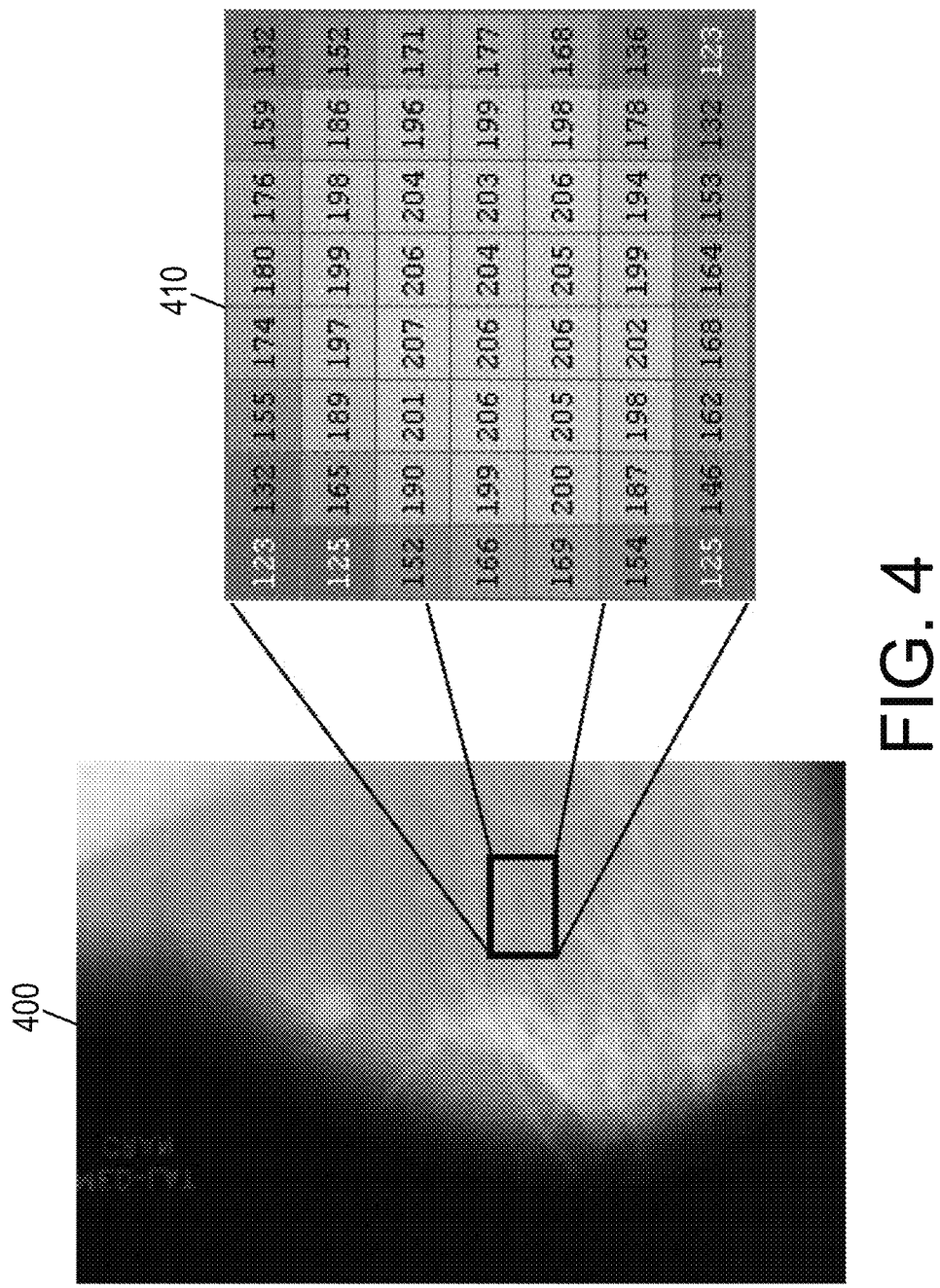
FIG. 4 illustrates an example selection of a region of interest within a mammogram image, according to some embodiments of the invention.

FIG. 4 illustrates an example selection of a region of interest 410 in a mammogram image 400, according to some embodiments of the invention. For simplicity, the region of interest 410 is 8 pixels by 7 pixels. Because mammograms are generally grayscale, each pixel in the region of interest 410 may be a shade of gray. In FIG. 4, each pixel is shown as a rectangle associated with a number, where that number indicates the gray level of that pixel. For instance, the gray level of a pixel may be the average of the red, blue, and green channels of the pixel. For an individual pixel, the red, blue, and green channels may be the same as one another for a true gray pixel, and in that case, the gray level may simply be the shared value of each of these channels. A lower gray level may indicate a darker shade of gray.

In FIG. 3, at block 310, a mathematical morphological filter may be applied to the region of interest 410 of the mammogram image 400. Existing mathematical morphological filters for digital image processing are known in the art and may be used. Generally, application of the mathematical morphological filter may reduce gray levels in a manner that potentially increases contrast in the region of interest 410.

Figures 5A, 5B:
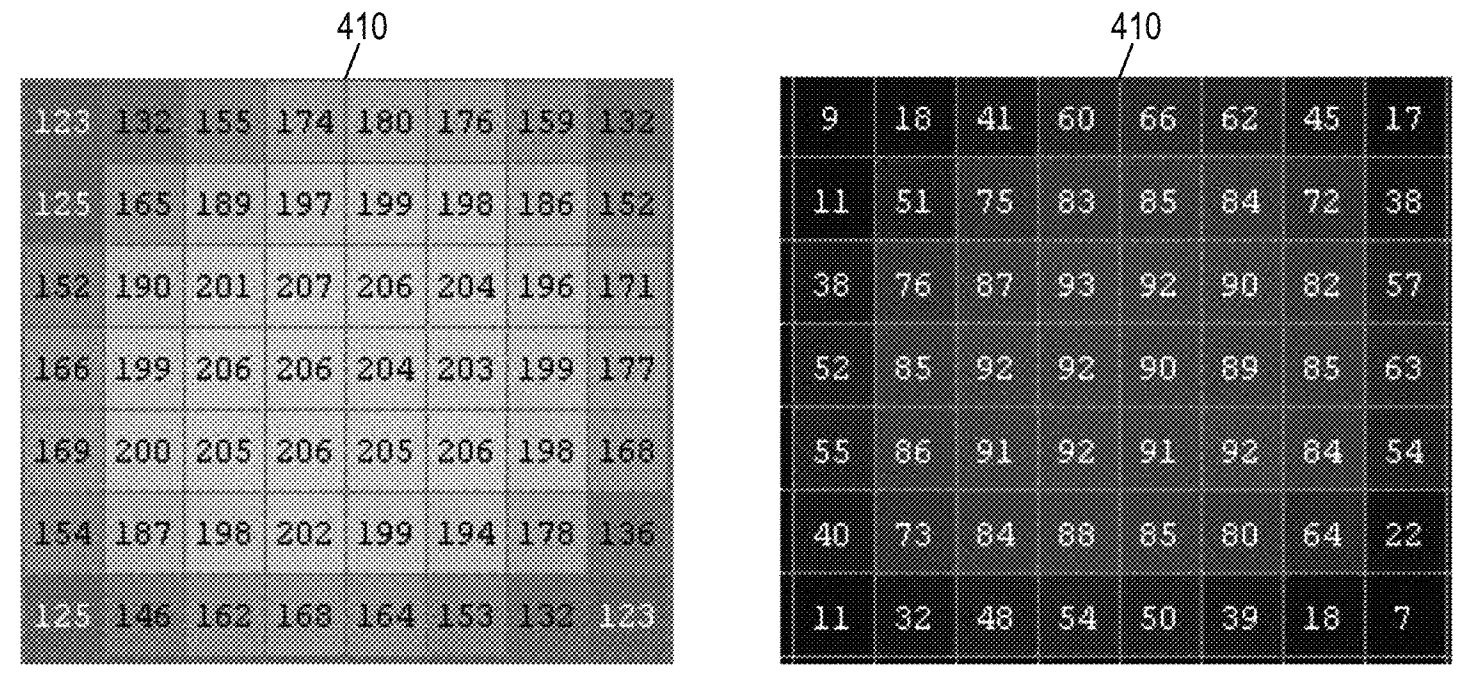

FIGS. 5A-5B illustrate an example application of the mathematical morphological filter, according to some embodiments of the invention. Specifically, FIG. 5A shows the original region of interest 410 selected from the mammogram image 400, while FIG. 5B shows the region of interest 410 after application of the mathematical morphological filter. Once again, each pixel is represented by a rectangle associated with the number that represents the gray level of the pixel. As shown, in this example, the gray levels are reduced by the application of the mathematical morphological filter.

In FIG. 3, at block 315, an entropy filter is applied to the region of interest 410 of the mammogram image 400. Existing entropy filters for digital image processing are known in the art and may be used. Generally, application of the entropy filter may indicate changes in gray levels across pixels, thus emphasizing portions where changes are minor and portions where changes are significant. Due to the nature of entropy filters, it may be the case that the result of the entropy filter has more pixels than the original region of interest 410.

Figures 6A, 6B:
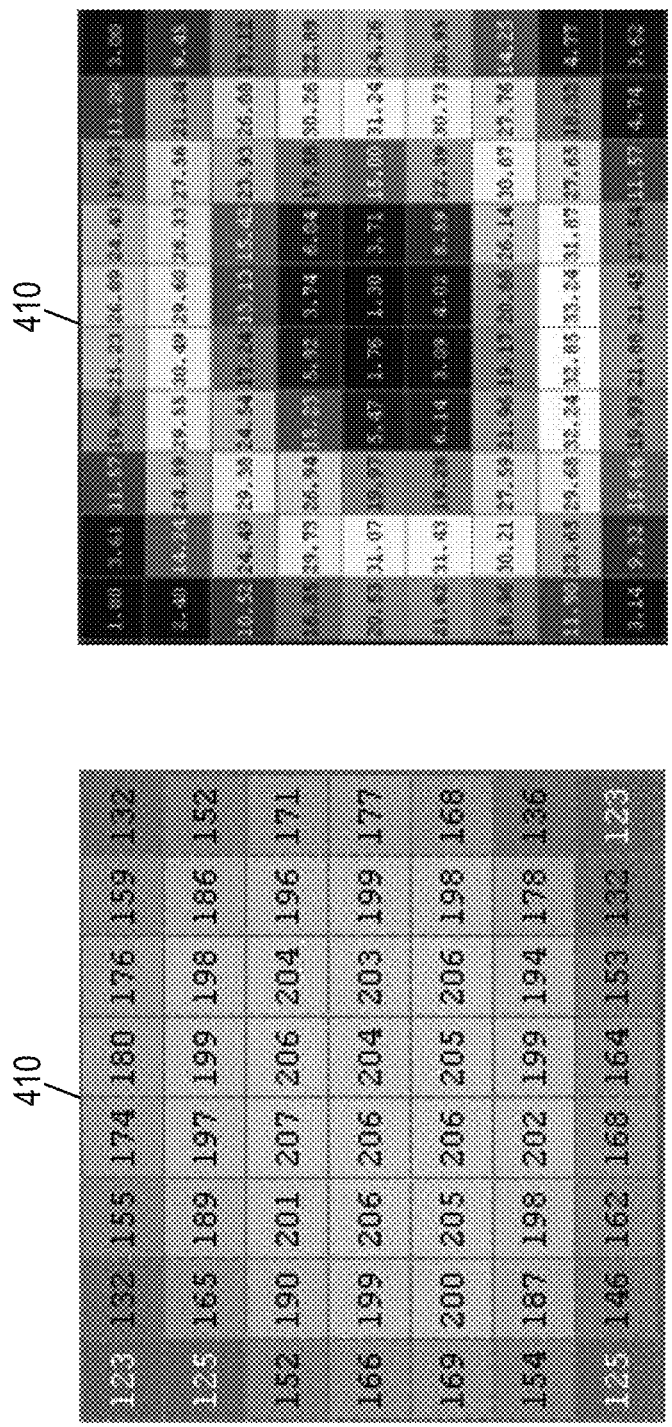
FIGS. 6A-6B illustrate an example application of an entropy filter, according to some embodiments of the invention.

FIGS. 6A-6B illustrate an example application of the entropy filter, according to some embodiments of the invention. Specifically, FIG. 6A shows the original region of interest 410 selected from the mammogram image 400, while FIG. 6B shows the region of interest 410 after application of the entropy filter. Once again, each pixel is represented by a rectangle associated with the number that represents the gray level of the pixel.

In FIG. 3, at block 320, application of a hybrid filter may be calculated for the region of interest 410, where the hybrid filter is based on both the mathematical morphological filter and the entropy filter. In some embodiments of the invention, the result of the hybrid filter may be an average of the result of the mathematical morphological filter and the entropy filter. More specifically, for each pixel, the result of the mathematical morphological filter may be a gray level, and the result of the entropy filter may be a gray level. Thus, the total result of the hybrid filter at a pixel may be the average of these two gray levels for the pixel. If the result of the entropy filter has a greater number of pixels than the result of the mathematical morphological filter and the original region of interest 410, then, for example, the value of the entropy filter used to determine the result of the hybrid filter at a particular pixel of the region of interest 410 may be deemed to be a weighted average of the corresponding pixels of the result of the entropy filter. It will be understood by one skilled in the art that other mechanisms may also be used to determine the hybrid filter based on the mathematical morphological filter and the entropy filter.

Figure 7:
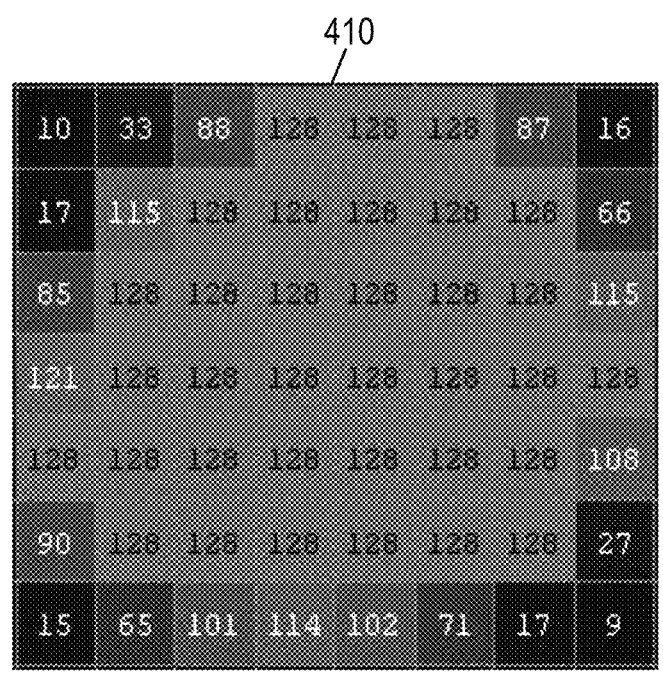
FIG. 7 illustrates an example application of a hybrid filter, according to some embodiments of the invention.

FIG. 7 illustrates an example application of the hybrid filter, according to some embodiments of the invention. Each pixel shown in the region of interest 410 is now associated with a gray level equal to the average of the gray levels in FIG. 5B and FIG. 6B, which respectively show the result of the mathematical morphological filter and the result of the entropy filter.

In FIG. 3, at block 325, the filtered region of interest may be returned as the result of applying the hybrid filter. If multiple regions of interest are identified within the mammogram image 400, then each filtered region of interest may be returned as an individual result of applying the hybrid filter. In that case, the visual recognition tool 140 may be applied to each such result at blocks 225-230 of the method 200 of recognizing a microcalcification.

Although recognition of microcalcifications may work with some success without the use of the hybrid filter, the hybrid filter may emphasize potential microcalcifications in mammogram images 400. As a result, the hybrid filer may improve the success rate of the screening system 100 in identifying microcalcifications. Further, in some embodiments of the invention, the hybrid filter is applied to the positive images and the negative images in the training data 135 as well, before the training data 135 is submitted to the visual recognition tool 140.

FIG. 8 is a block diagram of a computer system 800 for implementing some or all aspects of the system, according to some embodiments of this invention. The screening systems 100 and methods described herein may be implemented in hardware, software (e.g., firmware), or a combination thereof. In some embodiments, the methods described may be implemented, at least in part, in hardware and may be part of the microprocessor of a special or general-purpose computer system 800, such as a personal computer, workstation, minicomputer, or mainframe computer.

In some embodiments, as shown in FIG. 8, the computer system 800 includes a processor 805, memory 810 coupled to a memory controller 815, and one or more input devices 845 and/or output devices 840, such as peripherals, that are communicatively coupled via a local I/O controller 835. These devices 840 and 845 may include, for example, a printer, a scanner, a microphone, and the like. Input devices such as a conventional keyboard 850 and mouse 855 may be coupled to the I/O controller 835. The I/O controller 835 may be, for example, one or more buses or other wired or wireless connections, as are known in the art. The I/O controller 835 may have additional elements, which are omitted for simplicity, such as controllers, buffers (caches), drivers, repeaters, and receivers, to enable communications.

The I/O devices 840, 845 may further include devices that communicate both inputs and outputs, for instance disk and tape storage, a network interface card (NIC) or modulator/demodulator (for accessing other files, devices, systems, or a network), a radio frequency (RF) or other transceiver, a telephonic interface, a bridge, a router, and the like.

The processor 805 is a hardware device for executing hardware instructions or software, particularly those stored in memory 810. The processor 805 may be a custom made or commercially available processor, a central processing unit (CPU), an auxiliary processor among several processors associated with the computer system 800, a semiconductor-based microprocessor (in the form of a microchip or chip set), a macroprocessor, or other device for executing instructions. The processor 805 includes a cache 870, which may include, but is not limited to, an instruction cache to speed up executable instruction fetch, a data cache to speed up data fetch and store, and a translation lookaside buffer (TLB) used to speed up virtual-to-physical address translation for both executable instructions and data. The cache 870 may be organized as a hierarchy of more cache levels (L1, L2, etc.).

The memory 810 may include one or combinations of volatile memory elements (e.g., random access memory, RAM, such as DRAM, SRAM, SDRAM, etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 810 may incorporate electronic, magnetic, optical, or other types of storage media. Note that the memory 810 may have a distributed architecture, where various components are situated remote from one another but may be accessed by the processor 805.

The instructions in memory 810 may include one or more separate programs, each of which comprises an ordered listing of executable instructions for implementing logical functions. In the example of FIG. 8, the instructions in the memory 810 include a suitable operating system (OS) 811. The operating system 811 essentially may control the execution of other computer programs and provides scheduling, input-output control, file and data management, memory management, and communication control and related services.

Additional data, including, for example, instructions for the processor 805 or other retrievable information, may be stored in storage 820, which may be a storage device such as a hard disk drive or solid-state drive. The stored instructions in memory 810 or in storage 820 may include those enabling the processor to execute one or more aspects of the screening systems 100 and methods of this disclosure.

The computer system 800 may further include a display controller 825 coupled to a display 830. In some embodiments, the computer system 800 may further include a network interface 860 for coupling to a network 865. The network 865 may be an IP-based network for communication between the computer system 800 and an external server, client and the like via a broadband connection. The network 865 transmits and receives data between the computer system 800 and external systems. In some embodiments, the network 865 may be a managed IP network administered by a service provider. The network 865 may be implemented in a wireless fashion, e.g., using wireless protocols and technologies, such as WiFi, WiMax, etc. The network 865 may also be a packet-switched network such as a local area network, wide area network, metropolitan area network, the Internet, or other similar type of network environment. The network 865 may be a fixed wireless network, a wireless local area network (LAN), a wireless wide area network (WAN) a personal area network (PAN), a virtual private network (VPN), intranet or other suitable network system and may include equipment for receiving and transmitting signals.

Screening systems 100 and methods according to this disclosure may be embodied, in whole or in part, in computer program products or in computer systems 800, such as that illustrated in FIG. 8.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A computer-implemented method, comprising:
   receiving an image representing a patient, wherein the receiving the image representing the patient comprises selecting the image from a plurality of images in an image database, wherein the plurality of images represent a plurality of patients;
   applying a filter to the image to produce a filtered image, wherein the filter is a hybrid filter comprising a mathematical morphological filter and an entropy filter, and wherein applying the filter comprises:
      applying the mathematical morphological filter to a region of interest of the image;
      applying the entropy filter to the region of interest of the image; and
      calculating an average of a result of the mathematical morphological filter and a result of the entropy filter;
   submitting the filtered image to a visual recognition tool;
   determining, by the visual recognition tool, based on the filtered image, a score of the image, wherein the score indicates a likelihood that an abnormality appears in the image;
   assigning a respective score to each of the plurality of images; and
   ordering the plurality of images for review based on the respective scores of the plurality of images.

2. The computer-implemented method of claim 1, wherein the image is a mammogram image, and wherein the abnormality is a microcalcification.

3. The computer-implemented method of claim 1, further comprising training the visual recognition tool with a plurality of positive images known to show abnormalities and a plurality of negative images known to lack abnormalities.

4. The computer-implemented method of claim 1, further comprising:
   capturing, by an X-ray device, the image; and
   automatically storing the image in the image database.

5. A system comprising:
   a memory having computer-readable instructions; and
   one or more processors for executing the computer-readable instructions, the computer-readable instructions comprising:
      receiving an image representing a patient, wherein the receiving the image representing the patient comprises selecting the image from a plurality of images in an image database, wherein the plurality of images represent a plurality of patients;
      applying a filter to the image to produce a filtered image, wherein the filter is a hybrid filter comprising a mathematical morphological filter and an entropy filter, and wherein applying the filter comprises:
         applying the mathematical morphological filter to a region of interest of the image;
         applying the entropy filter to the region of interest of the image; and calculating an average of a result of the mathematical morphological filter and a result of the entropy filter;

submitting the filtered image to a visual recognition tool;

determining, by the visual recognition tool, based on the filtered image, a score of the image, wherein the score indicates a likelihood that an abnormality appears in the image;

assigning a respective score to each of the plurality of images; and ordering the plurality of images for review based on the respective scores of the plurality of images.

6. The system of claim 5, wherein the image is a mammogram image, and wherein the abnormality is a microcalcification.

7. The system of claim 5, the computer-readable instructions further comprising training the visual recognition tool with a plurality of positive images known to show abnormalities and a plurality of negative images known to lack abnormalities.

8. The system of claim 5, the computer-readable instructions further comprising:

capturing, by an X-ray device, the image; and automatically storing the image in the image database.

9. A computer-program product for screening one or more mammograms, the computer-program product comprising a computer-readable storage medium having program instructions embodied therewith, the program instructions executable by a processor to cause the processor to perform a method comprising:

receiving an image representing a patient, wherein the receiving the image representing the patient comprises selecting the image from a plurality of images in an image database, wherein the plurality of images represent a plurality of patients;

applying a filter to the image to produce a filtered image, wherein the filter is a hybrid filter comprising a mathematical morphological filter and an entropy filter, and wherein applying the filter comprises:

applying the mathematical morphological filter to a region of interest of the image;

applying the entropy filter to the region of interest of the image; and calculating an average of a result of the mathematical morphological filter and a result of the entropy filter;

submitting the filtered image to a visual recognition tool;

determining, by the visual recognition tool, based on the filtered image, a score of the image, wherein the score indicates a likelihood that an abnormality appears in the image;

assigning a respective score to each of the plurality of images; and ordering the plurality of images for review based on the respective scores of the plurality of images.

10. The computer-program product of claim 9, wherein the image is a mammogram image, and wherein the abnormality is a microcalcification.

11. The computer-program product of claim 9, the method further comprising training the visual recognition tool with a plurality of positive images known to show abnormalities and a plurality of negative images known to lack abnormalities.

* * * * *